US012588960B2

(12) United States Patent
Sudre et al.

(10) Patent No.: US 12,588,960 B2
(45) Date of Patent: Mar. 31, 2026

(54) MEDICAL ROBOT FOR PLACEMENT OF MEDICAL INSTRUMENTS UNDER ULTRASOUND GUIDANCE

(71) Applicant: Quantum Surgical, Montpellier (FR)

(72) Inventors: Mathieu Sudre, Restinclières (FR);
Lucien Blondel, Montpellier (FR);
Bertin Nahum, Castelnau-le-Lez (FR);
Fernand Badano, Lyons (FR)

(73) Assignee: Quantum Surgical, Montpellier (FR)

( * ) Notice: Subject to any disclaimer, the term of this patent is extended or adjusted under 35 U.S.C. 154(b) by 197 days.

(21) Appl. No.: 18/571,467

(22) PCT Filed: Jun. 14, 2022

(86) PCT No.: PCT/FR2022/051136
§ 371 (c)(1),
(2) Date: Dec. 18, 2023

(87) PCT Pub. No.: WO2022/263763
PCT Pub. Date: Dec. 22, 2022

(65) Prior Publication Data
US 2024/0350208 A1 Oct. 24, 2024

(30) Foreign Application Priority Data

Jun. 16, 2021 (FR) ...................................... 2106350

(51) Int. Cl.
*A61B 34/30* (2016.01)
*A61B 90/11* (2016.01)
(Continued)

(52) U.S. Cl.
CPC .............. *A61B 34/30* (2016.02); *A61B 90/11* (2016.02); *A61B 2034/107* (2016.02);
(Continued)

(58) Field of Classification Search
CPC ... A61B 34/30; A61B 90/11; A61B 2034/107;
A61B 2034/2063; A61B 2090/364;
(Continued)

(56) References Cited

U.S. PATENT DOCUMENTS 6,546,279 B1 4/2003 Bova et al.
2008/0287794 A1* 11/2008 Li ........................... A61B 34/20
600/439
(Continued)

FOREIGN PATENT DOCUMENTS

WO 2021099729 A1 5/2021

OTHER PUBLICATIONS

International Search Report in PCT/FR2022/051136, mailed Sep. 16, 2022, 10 pages.
(Continued)

*Primary Examiner* — Bao Long T Nguyen
(74) *Attorney, Agent, or Firm* — ArentFox Schiff LLP

(57) ABSTRACT

A medical robot (10) comprises a robotic arm (13) equipped with a tool guide (14) for guiding a medical instrument (15) along a trajectory defined by an entry point at the patient's skin and a target point at a lesion to be treated in an anatomy of interest of the patient. The medical robot cooperates with an ultrasound probe (40) and with a navigation system (30) for determining the position of the robot, the position of the ultrasound probe, and the position of a patient marker (22). The robot is configured to generate a model of the position of the target point and the position of the entry point according to the position of the patient marker on the basis of ultrasound images acquired by the ultrasound probe during at least one respiratory cycle of the patient. The model thus generated then allows the robotic arm to be
(Continued)

Figure 1:
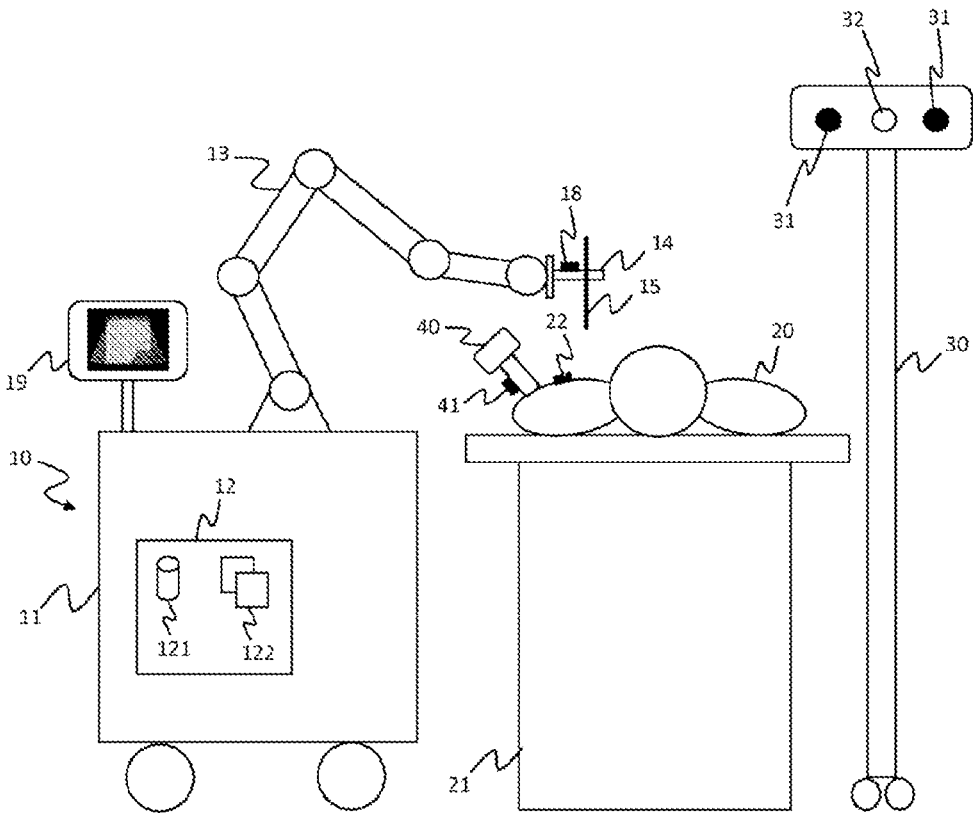

controlled in real time according to the position of the patient marker in order to guide the medical instrument with precision.

15 Claims, 11 Drawing Sheets

(51) Int. Cl.

| | | |
|---|---|---|
| *A61B 34/10* | | (2016.01) |
| *A61B 34/20* | | (2016.01) |
| *A61B 90/00* | | (2016.01) |

(52) U.S. Cl.
CPC . *A61B 2034/2063* (2016.02); *A61B 2090/364* (2016.02); *A61B 2090/378* (2016.02); *A61B 2090/3925* (2016.02)

(58) Field of Classification Search
CPC ...... A61B 2090/378; A61B 2090/3925; A61B 34/32; A61B 34/20; A61B 34/25; A61B 2017/00699; A61B 2034/2055; A61B 2034/2059; A61B 2090/064; A61B 2090/3966; A61B 2034/105; A61B 34/10; A61B 90/39; B25J 9/1664

See application file for complete search history.

(56) References Cited

U.S. PATENT DOCUMENTS

| | | | |
|---|---|---|---|
| 2014/0316247 | A1 | 10/2014 | Hwang et al. |
| 2018/0092628 | A1* | 4/2018 | Mine ..................... A61B 8/465 |

OTHER PUBLICATIONS

Written Opinion in PCT/FR2022/051136, mailed Sep. 16, 2022, 13 pages.

* cited by examiner

MEDICAL ROBOT FOR PLACEMENT OF MEDICAL INSTRUMENTS UNDER ULTRASOUND GUIDANCE

CROSS-REFERENCE TO RELATED APPLICATIONS

This application is a National Phase of PCT/FR2022/051136, filed on Jun. 14, 2022, which claims priority to FR Patent Application No. 2106350, filed on Jun. 16, 2021, the disclosures of which are hereby incorporated by reference in their entireties.

FIELD OF THE INVENTION

The present invention belongs to the field of robotic devices for assisting a practitioner during a minimally invasive medical intervention comprising the insertion of one or more medical instruments into an anatomy of interest of a patient. In particular, the invention relates to a medical robot configured to track the movement of a target point in a lesion within a patient's anatomy of interest and to adjust in real time the position of an articulated arm of the robot in order to optimally guide a medical instrument to the target point. The movement of the target point may be generated in particular by the patient's breathing, or by the insertion of the medical instrument.

PRIOR ART

To prepare for a minimally invasive intervention aimed at reaching a target anatomical region in a patient's anatomy of interest using a medical instrument, a practitioner generally performs intervention planning based on a pre-operative medical image (obtained a few days or weeks before the intervention) or pre-interventional medical image (obtained just before the intervention, when the patient is on the intervention table). The minimally invasive medical intervention may be aimed in particular at performing the biopsy or ablation of a tumor in an organ, at performing a vertebroplasty or a cementoplasty, or even at stimulating a particular anatomical region. The anatomy of interest can be, for example, a lung, a kidney, the liver, the brain, a tibia, a knee, a vertebra, etc. The medical instrument may be a needle, a probe, a catheter, etc.

During this planning step, the practitioner defines a target point in a region of the anatomy of interest to be treated. The practitioner also defines an entry point for the medical instrument on the patient's skin. These two points then define a trajectory that the medical instrument must follow in order to carry out the medical intervention. In the particular case of the soft organs situated in the thoracic region, the abdominal region or the pelvic region, the movements linked to the patient's breathing and/or the local deformations of the organ due to the insertion of the medical instrument cause a displacement of the target point during the intervention. Pre-operative or pre-interventional medical planning images do not predict this displacement of the target point during the intervention. Thus, the position of the target point (i.e. the position of the region to be treated in the anatomy of interest) is usually different during the acquisition of the medical planning image and during the intervention. Therefore, when the insertion of the medical instrument is planned from the medical planning image, there is a risk that the target point will not be reached with precision by the medical instrument.

In addition, there is a risk that the medical instrument will bend during insertion and will not reach the target point if the planned trajectory to be followed by the medical instrument is not adjusted accordingly.

In order to limit the displacement of the target point generated by the patient's breathing, it is conceivable, at the time of insertion of the medical instrument, to block the patient's breathing at a phase of the respiratory cycle corresponding to that at which the medical planning image was acquired. Breathing may be blocked voluntarily by the patient if the medical intervention takes place under local anesthesia, or else in a controlled manner by the practitioner if the medical intervention takes place under general anesthesia (interruption of mechanical ventilation). However, this solution is not always very accurate because it is difficult to obtain an exact correspondence between the phase of the respiratory cycle at which the medical planning image was acquired and the phase of the respiratory cycle at which the patient's breathing is blocked during the intervention. Furthermore, this solution presupposes a relatively rapid insertion of the medical instrument, since this must be done while the patient's breathing is blocked.

It is also conceivable to take several medical planning images during a respiratory cycle of the patient and to determine the trajectory least subject to the deformations and displacements of the anatomy of interest that are generated by respiration. However, there is again a risk that the target point will not be reached with precision by the medical instrument.

It is also possible to track the position of the target point throughout the intervention, by regularly acquiring intra-interventional medical images (images acquired when the medical instrument is inserted into the patient's body). These medical images are usually acquired by computed tomography, X-rays or magnetic resonance. In the case of computed tomography or X-rays, however, such a solution has the drawback of significantly irradiating the patient and the practitioner during the intervention. In the case of magnetic resonance imaging, it is necessary to use specific non-magnetic material, in particular for the anesthetic material, which is particularly restrictive. This solution also requires the use of bulky imaging devices throughout the intervention.

It is also known to track the position of a lesion within an anatomy of interest with the aid of ultrasound images. However, the lesion is not always visible on an ultrasound image, and existing solutions generally lack precision.

It is still therefore necessary to find a solution for inserting a medical instrument accurately at a target point of a region to be treated within an anatomy of interest of a patient, in particular when the movements linked to the patient's breathing and/or the local deformations of the anatomy of interest due to the insertion of the medical instrument cause a displacement of the target point during the intervention.

DESCRIPTION OF THE INVENTION

The object of the devices and methods disclosed in the present application is to remedy all or some of the drawbacks of the prior art, in particular those set out above.

To this end, and according to a first aspect, there is proposed a medical robot for assisting a practitioner during a medical intervention to treat a lesion in an anatomy of interest of a patient. The medical robot comprises a robotic arm comprising at a distal end a tool guide for guiding a medical instrument. The medical robot also comprises a control unit configured to control the robotic arm. The medical robot is configured to cooperate with a navigation system and with an ultrasound probe to be positioned by the practitioner at the anatomy of interest of the patient. The control unit is configured to be able to determine at any time, on the basis of information communicated by the navigation system, the position of a robot marker intended to be fixed on the medical robot, the position of a patient marker intended to be positioned on the patient in the vicinity of the anatomy of interest, and the position of a probe marker to be fixed on the ultrasound probe. During a modeling phase, the control unit is configured to receive a plurality of ultrasound images acquired by the ultrasound probe during at least one respiratory cycle of the patient and to generate, from said ultrasound images, a model for estimating the position of a target point at the lesion and the position of an entry point at the patient's skin, based on the position of the patient marker, irrespective of the moment considered in the patient's respiratory cycle. During a guidance phase, the control unit is configured to control the robotic arm in real time based on the position of the patient marker in order to guide the medical instrument along a trajectory defined by the position of the target point and the position of the entry point associated with the position of the patient marker in the model.

In the present application, the term "position" must be understood in the broad sense as describing both the position and the orientation of an object in a three-dimensional frame of reference (the term "pose" is sometimes used in the English-language literature). The marker positions (patient marker, robot marker and probe marker) and also the position of the target point and the position of the entry point can be defined in a robot reference frame or in a navigation system reference frame. It should be noted that the reference frame of the robot can be defined relative to the reference frame of the navigation system because the position of the robot marker is known both in the reference frame of the navigation system and in the reference frame of the robot (each articulation of the robotic arm comprises, for example, an encoder making it possible to know the position of each articulated element of the robotic arm in the reference frame of the robot, and the position of the robot marker on the robot is known a priori by the control unit).

The modeling phase takes place at the beginning of the intervention, before bringing the robotic arm closer to the anatomy of interest and before inserting the medical instrument into the patient's body. The modeling phase is used to model the movement of the target point and the movement of the entry point relative to the patient marker during a respiratory cycle. During the modeling phase, the positions of the target point and the positions of the entry point are correlated with the positions of the patient marker, and it is thus possible to define the position of the target point and the position of the entry point according to the position of the patient marker. The model obtained therefore makes it possible to define, at any instant of the respiratory cycle, the position of the target point and the position of the entry point which correspond to the trajectory that the medical instrument has to follow in order to reach the target point with precision.

Once the position of the target point and the position of the entry point are modeled according to the position of the patient marker, it becomes possible, by tracking the position of the patient marker in real time using the navigation system, to define in real time the position to be taken by the robotic arm in order for the medical instrument to be guided along the trajectory defined by the position of the target point and the position of the entry point associated with the position of the patient marker. This real-time tracking may in particular take place before the insertion of the medical instrument.

With such arrangements, it becomes possible to block the patient's breathing at any instant of the respiratory cycle in order to proceed with the insertion of the medical instrument. Indeed, irrespective of the instant at which the patient's breathing is blocked, the robotic arm will be correctly positioned to allow the insertion of the medical instrument along the desired trajectory.

Moreover, it is no longer necessary to block the patient's breathing during the intervention. Indeed, the robotic arm is moved in real time so that the position of the robotic arm is constantly adjusted in order to guide the medical instrument along the desired trajectory.

The invention also makes it possible to minimize lateral readjustments of the trajectory after insertion of the medical instrument (such lateral readjustments of the trajectory are generally traumatic for the organ traversed by the medical instrument).

The medical instrument can thus be inserted with very great precision at the region to be treated, irrespective of the instant at which the medical instrument is inserted during the respiratory cycle. The insertion of the medical instrument is generally carried out by the practitioner, the object of the medical robot being to guide the insertion of the medical instrument by the practitioner. However, nothing would prevent the insertion of the medical instrument from being automated and controlled by the control unit.

Furthermore, since the modelling of the position of the target point and of the position of the entry point during a respiratory cycle is carried out on the basis of ultrasound images, the patient and the practitioner are not exposed to ionizing radiation during the intervention.

In particular embodiments, the invention may further comprise one or more of the following features, taken in isolation or according to all technically possible combinations.

In particular embodiments, during the modeling phase, the control unit is configured, for each ultrasound image received, to:
  determine the position of the patient marker and the position of the probe marker at the time when said ultrasound image was acquired by the ultrasound probe,
  obtain an analysis image, from the ultrasound image, on which the lesion is visible,
  determine, on the analysis image, a target point at the lesion and an entry point at the patient's skin, the target point and the entry point thus defining a trajectory to be followed for the medical instrument,
  determine the position of the target point and the position of the entry point from the position of the probe marker,
  establish an association between the position of the patient marker, the position of the target point and the position of the entry point thus determined for said ultrasound image.
Furthermore, the control unit is configured to model, from the information thus obtained for the plurality of ultrasound images, the position of the target point and the position of the entry point, as a function of the position of the patient marker, irrespective of the moment considered in a respiratory cycle of the patient.

In particular embodiments, during the guidance phase, upon insertion of the medical instrument, the control unit is configured to regularly receive new ultrasound images acquired by the ultrasound probe. The control unit is further configured to update the model based on said new ultrasound images.

As soon as the practitioner begins to insert the medical instrument into the patient's body, the position of the entry point at the patient's skin is fixed and becomes a pivot of rotation for the movements of the robotic arm. However, it is still possible to track in real time the position of the target point, the position of the entry point, and the position of the patient marker with new ultrasound images acquired in real time during the phase of insertion of the medical instrument. Such arrangements make it possible to take into account any movement of the target point resulting from the insertion of the medical instrument. The target point can in fact move in the direction of the trajectory followed by the medical instrument during its insertion (this is particularly the case when the target point to be reached is in a lesion, for example a tumor, within a soft organ). The real-time determination of the position of the target point with the aid of the ultrasound images makes it possible to update in real time the trajectory to be followed by the medical instrument, and also the position of the robotic arm in order to guide the medical instrument along this trajectory.

In particular embodiments, during the guidance phase, upon insertion of the medical instrument, the control unit is further configured to determine, for each new ultrasound image received, the position of the medical instrument, and to adjust the real-time control of the robotic arm according to the position of the medical instrument.

Such arrangements make it possible to take into account the risk of the medical instrument bending during insertion and to adjust the real-time control of the robotic arm accordingly (the trajectory to be followed by the medical instrument is then no longer a straight line between the entry point and the target point).

In particular embodiments, the analysis image corresponds directly to the ultrasound image. This is particularly the case when the lesion is visible on the ultrasound image.

In particular embodiments, the control unit is configured to obtain the analysis image by merging the ultrasound image with a pre-operative or pre-interventional reference image on which the lesion is visible.

Indeed, when the lesion is not visible on an ultrasound image (isoechogenic lesion), it is not possible to determine the position of the target point directly on the ultrasound image. The ultrasound image should then be registered with a reference image of a different modality on which the lesion is visible. It may be in particular a pre-operative or pre-interventional image obtained by computed tomography, positron emission tomography or magnetic resonance imaging. The merging of the ultrasound image with the reference image then gives an analysis image on which the lesion is visible. The registration can be global (registration on the entire anatomy of interest) or local (optimized registration on a particular region of the anatomy of interest). The registration can be done rigidly (by translation and/or rotation) or non-rigidly (with deformation). The registration can in particular be implemented by an automatic learning algorithm based on the recognition of particular anatomical structures on the images that are to be merged.

In particular embodiments, a radiopaque element of the patient marker is visible on the reference image, and the control unit is configured to merge the ultrasound image with the reference image by registration based on the position of the patient marker relative to the position of the probe marker at the time when the ultrasound image was acquired by the ultrasound probe.

In particular embodiments, the reference image is a computed tomography image, a positron emission tomography image, or a magnetic resonance imaging image.

In particular embodiments, the ultrasound images received from the ultrasound probe are B-mode ultrasound images.

In particular embodiments, the control unit is configured to receive and process ultrasound images acquired by the ultrasound probe at a rate of at least fifteen images per second.

Such arrangements make it possible to guarantee real-time tracking of the position of the target point and consequently real-time adjustment of the position of the robotic arm so that the medical instrument is guided along the desired trajectory throughout the intervention.

In particular embodiments, the medical robot further comprises a user interface comprising a display screen enabling the practitioner to view the analysis images.

In particular embodiments, the user interface comprises input means enabling the practitioner to identify, on an analysis image displayed on the display screen, a target point and/or an entry point and/or an anatomical region that is not to be traversed by the medical instrument.

The practitioner can thus plan the intervention, using the user interface, on a pre-interventional image corresponding to an analysis image associated with a first ultrasound image acquired by the ultrasound probe (it can be directly the ultrasound image, if the lesion is visible on the ultrasound image, or otherwise a fusion image resulting from the registration of the ultrasound image with a pre-operative image of a different modality on which the lesion is visible). The target point and the entry point defined by the practitioner on this first image are then determined automatically by the control unit on the following analysis images. The tracking of the target point can in particular be implemented by a method of tracking movement in several successive ultrasound images, by a "speckle" deformation analysis or by an artificial intelligence algorithm ("speckle" represents the set of small, rapidly fluctuating spots that appear in the instant texture of an image and that give it a grainy appearance.) When the lesion is not visible on the ultrasound image, in order to assist in tracking the target point on the analysis images, it is advantageous to track the movement of an anatomical structure close to the lesion visible on ultrasound images (for example a blood vessel).

In particular embodiments, the user interface comprises an augmented reality device for superimposing the analysis images with actual images of the patient's body on the display screen.

The augmented reality device makes it possible to superimpose on the patient's body the moving and three-dimensional lesion, and also the progression of the medical instrument during its insertion. It may be, for example, a screen positioned on the intervention table above the patient, or else a mask, a helmet or augmented reality glasses. This type of display facilitates the spatial representation of the anatomy of interest of the patient by the practitioner.

In particular embodiments, the control unit is configured to compare an ultrasound image with a reference image on which the lesion is visible, and to give an indication to the practitioner of the direction in which the ultrasound probe should be moved so that an ultrasound image acquired by the ultrasound probe comprises an anatomical region in which the lesion is located.

The reference image is, for example, a pre-operative or pre-interventional image obtained by computed tomography, positron emission tomography or magnetic resonance imaging. The direction in which the ultrasound probe should be moved is for example indicated to the practitioner on the display screen of the user interface. According to other examples, the direction in which the ultrasound probe should be moved may be indicated to the practitioner by light signals or by haptic feedback (vibrations) at the ultrasound probe, or else on an augmented reality display.

According to a second aspect, there are proposed a medical device comprising a medical robot according to any one of the embodiments described above, and also a navigation system and an ultrasound probe that are intended to cooperate with the medical robot.

OVERVIEW OF THE FIGURES

Figure 2:
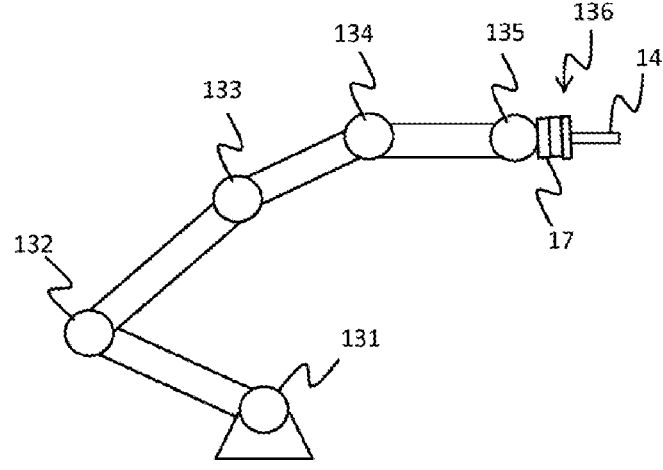
Figure 3:
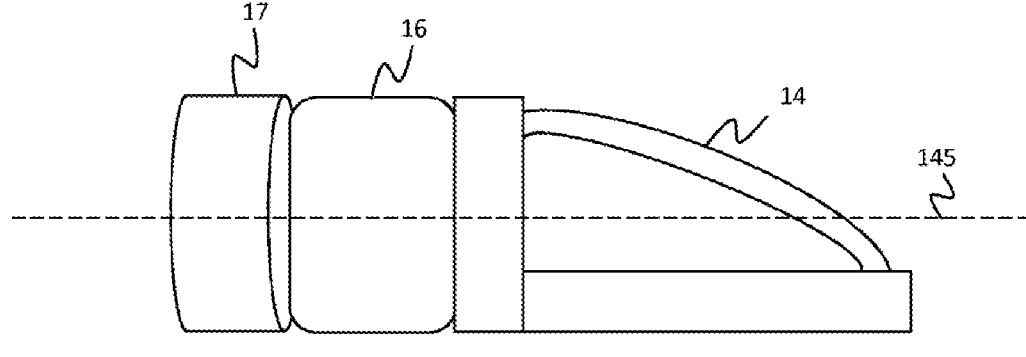
Figure 4:
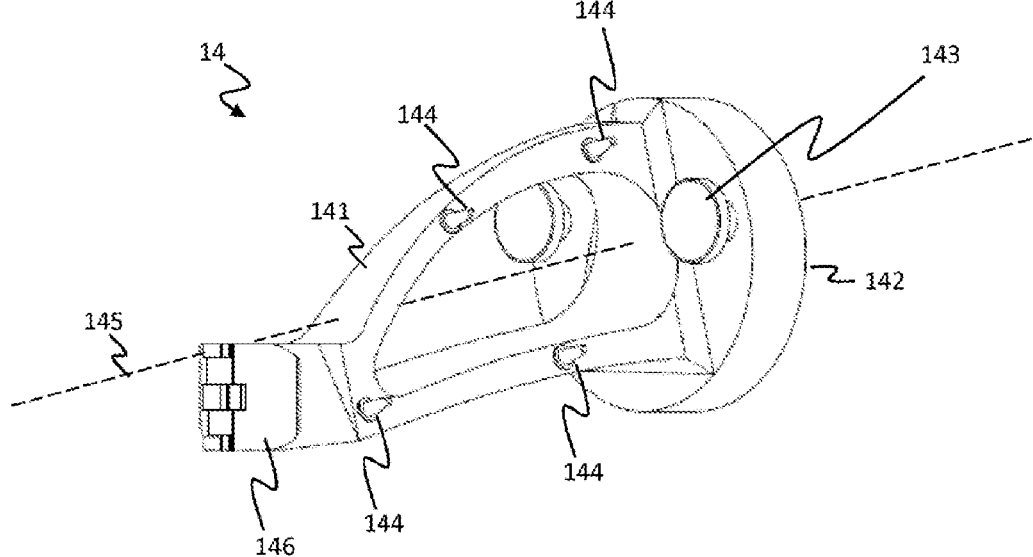
Figure 5:
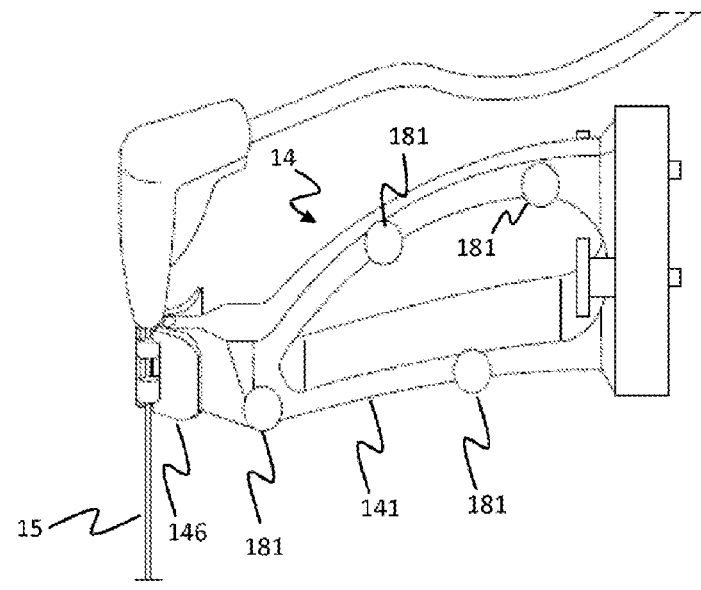
Figure 6:
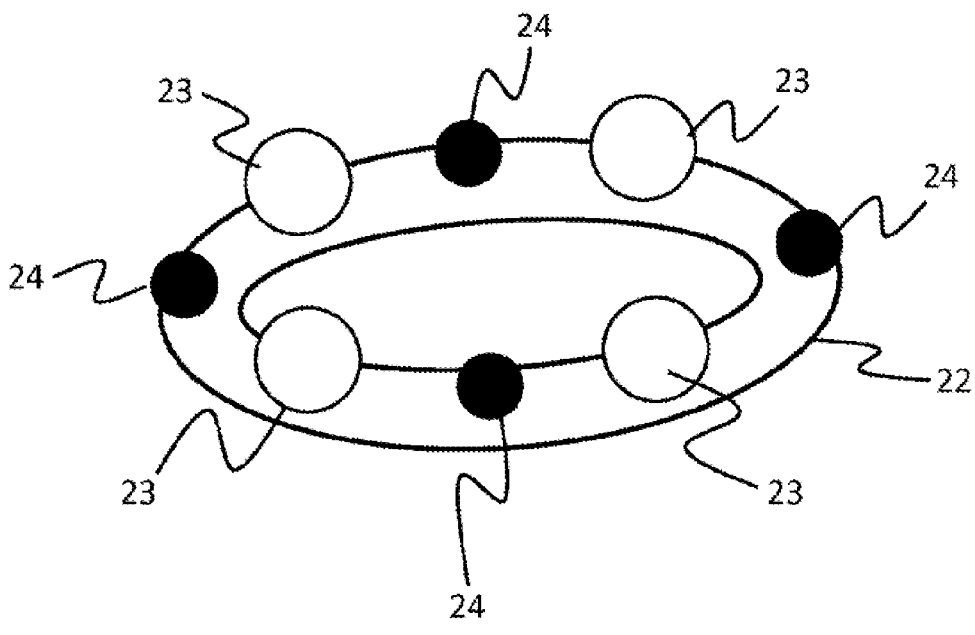
Figure 7:
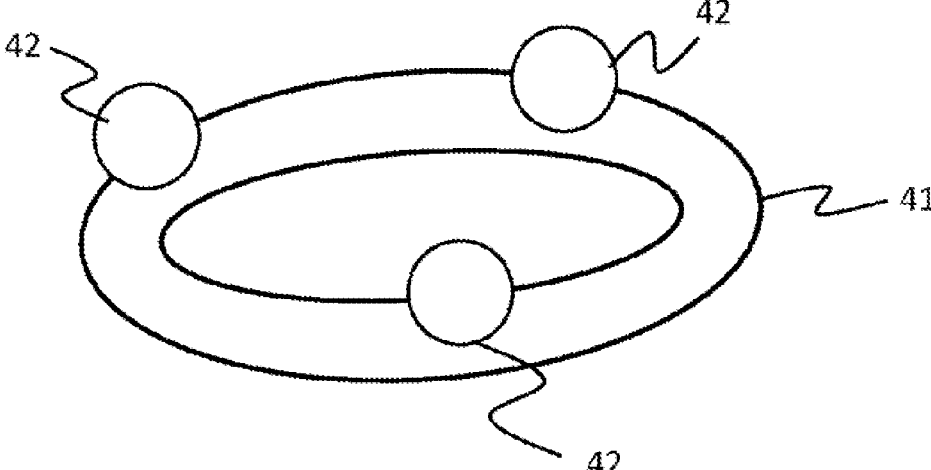
Figure 8:
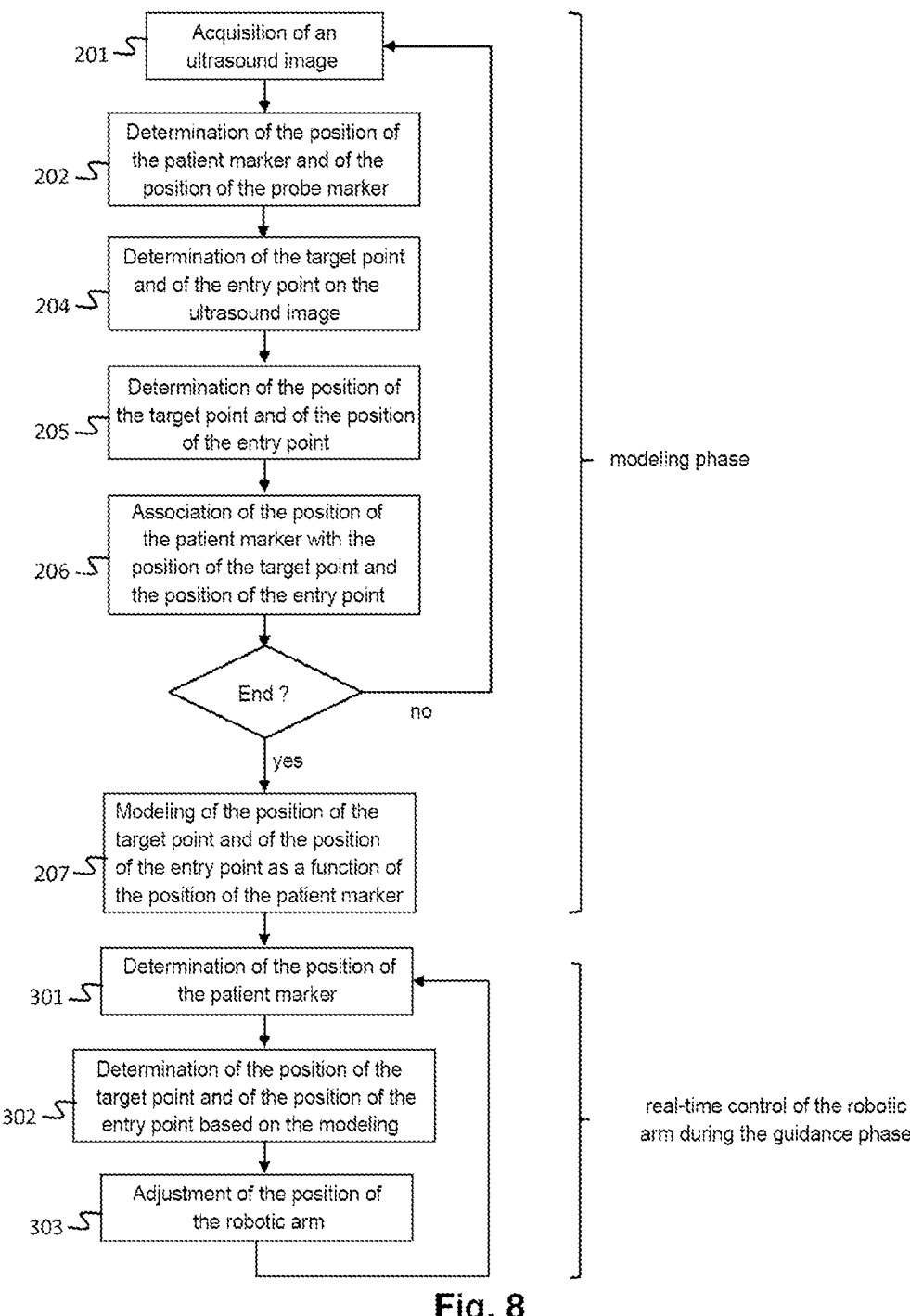
Figure 9:
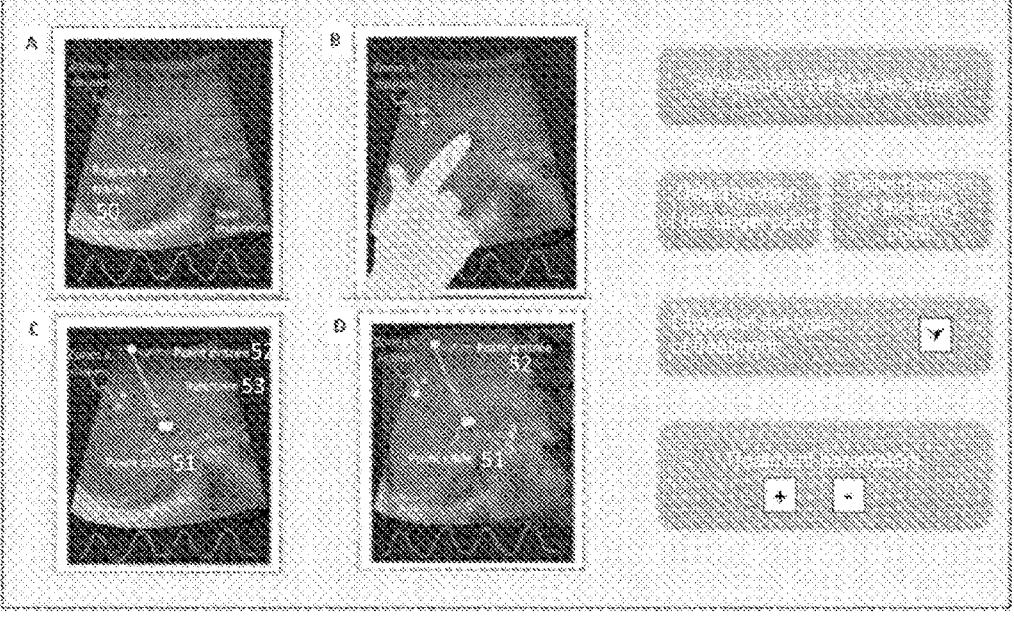
Figure 10:
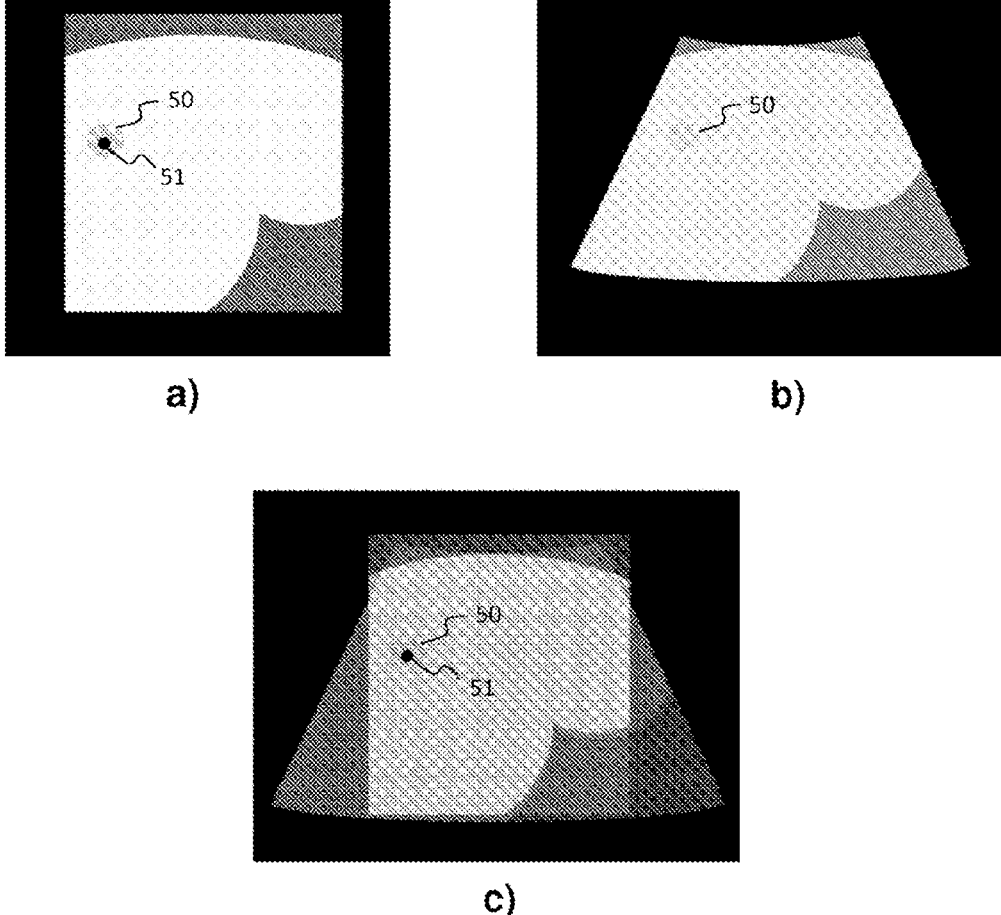
Figure 11:
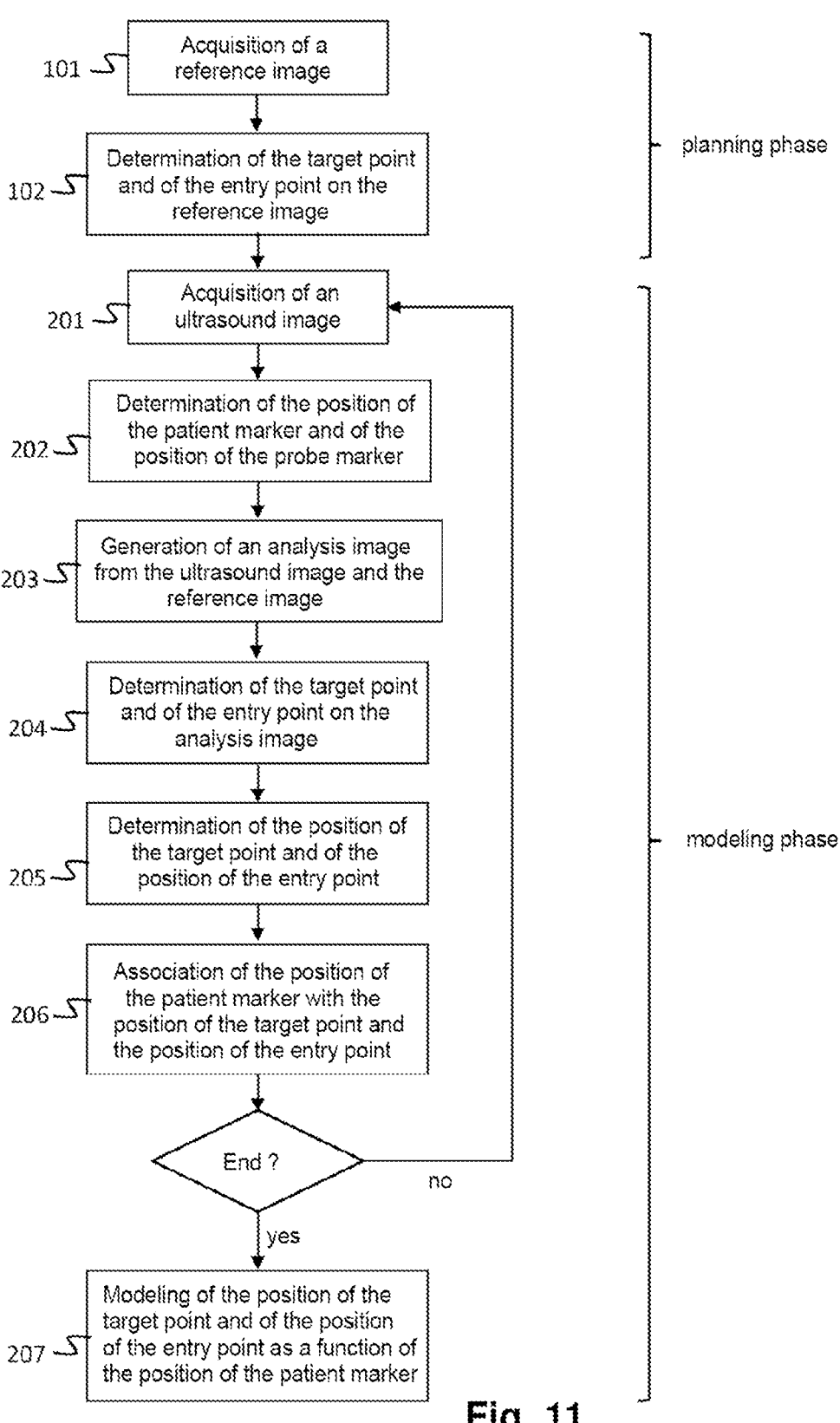
Figure 12:
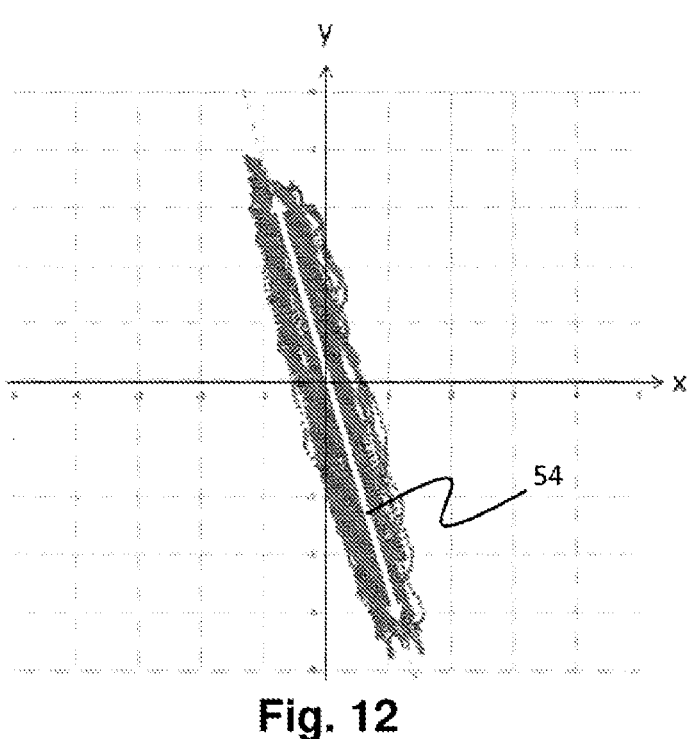
Figure 13:
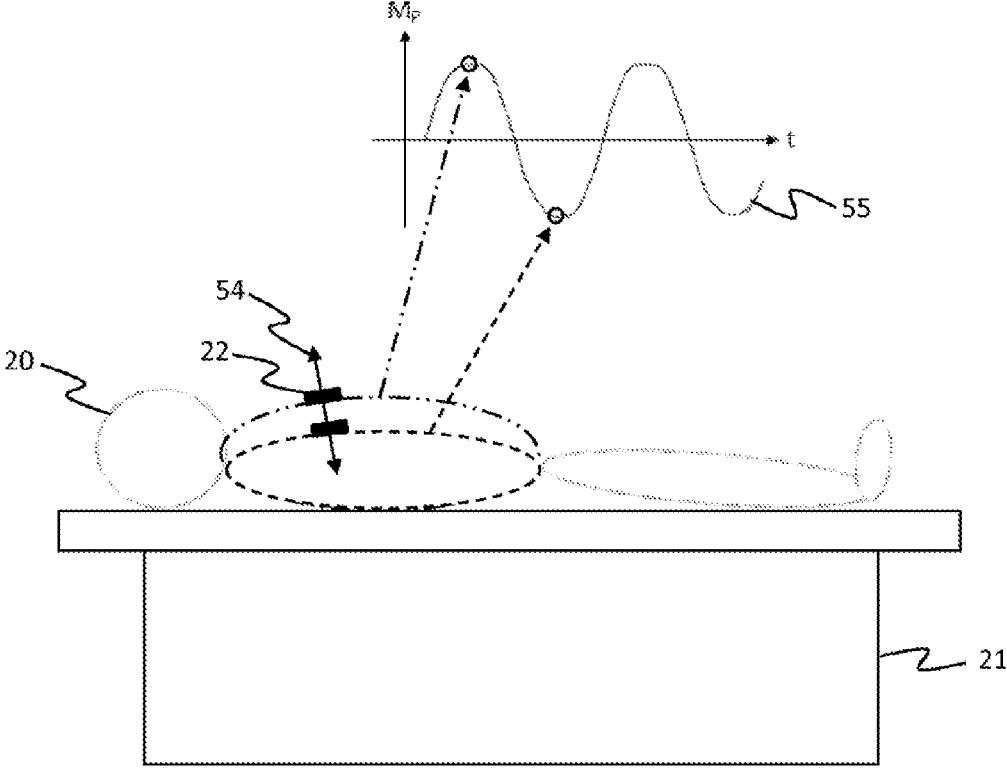
Figure 14:
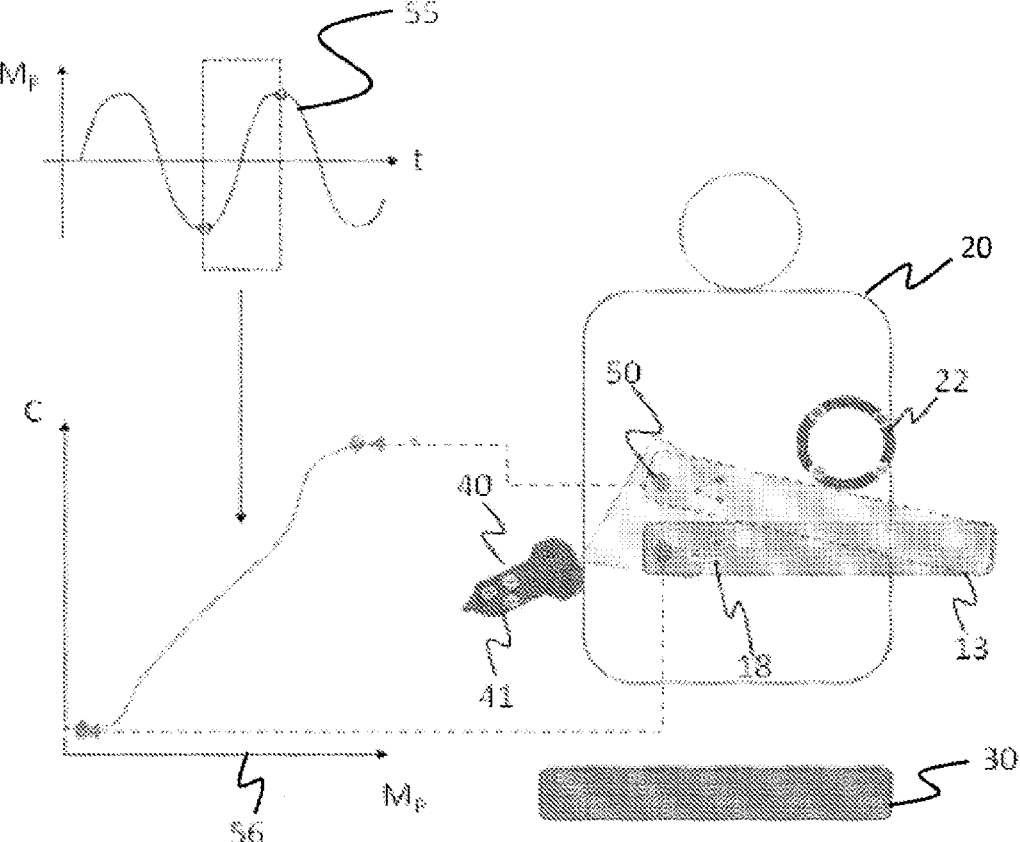
Figure 15:
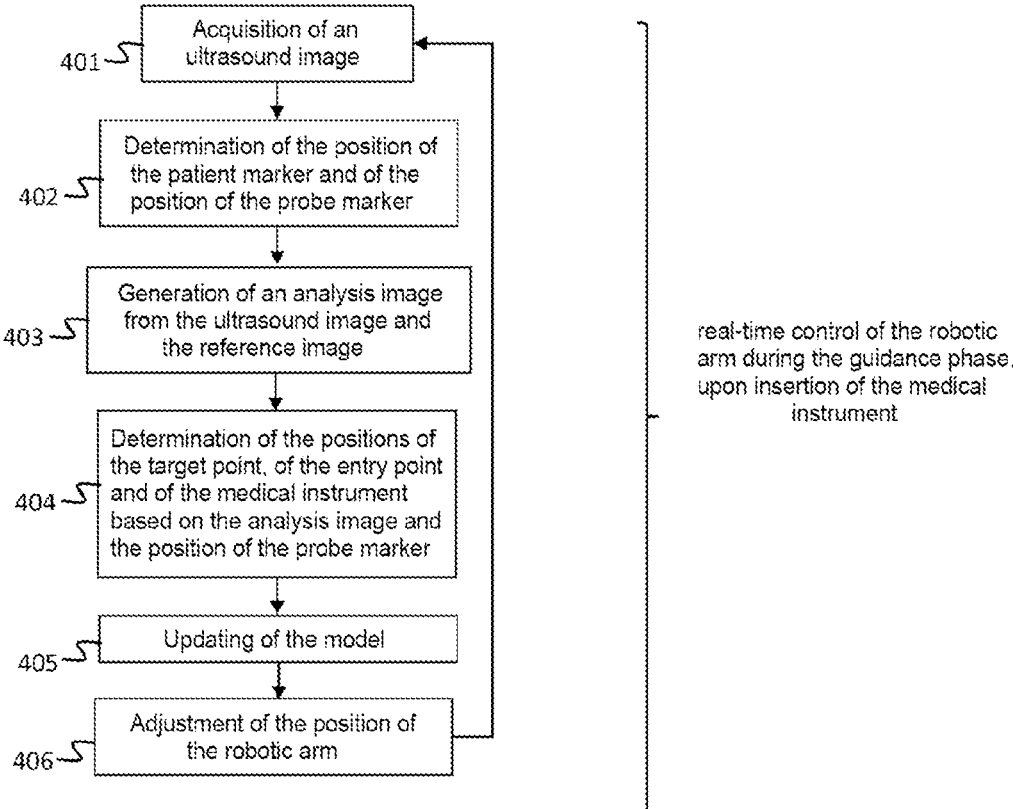

The invention will be better understood on reading the following description, given by way of non-limiting example, and given with reference to FIGS. 1 to 15, which show:

FIG. 1 a schematic representation of a medical device according to the invention comprising a medical robot, a navigation system and a probe, FIG. 2 a schematic representation of the robotic arm of the medical robot, FIG. 3 a schematic representation of the tool guide intended to be attached to the end of the robotic arm, FIG. 4 a representation of the tool guide showing a device for holding a medical instrument at the end of the tool guide, FIG. 5 a representation of the tool guide showing the positioning of the medical instrument on the tool guide, and also elements detectable by a navigation system forming a "robot marker", FIG. 6 a schematic representation of a "patient marker" intended to be positioned on the patient near the anatomy of interest, FIG. 7 a schematic representation of a "probe marker" intended to be attached to the ultrasound probe, FIG. 8 a schematic representation of the main steps of a method implemented by the control unit during a modeling phase (in the case where the lesion is visible on the ultrasound images), then during a phase of real-time control of the robotic arm before the insertion of the medical instrument, FIG. 9 a schematic representation of a user interface enabling the practitioner to identify on an image a target point and/or an entry point and/or a region at risk, and also treatment parameters, FIG. 10 a schematic representation of a pre-operative or pre-interventional image (part a) of the figure), an ultrasound image (part b) of the figure), and a fusion image resulting from the registration of the pre-operative or pre-interventional image and the ultrasound image (part c) of the figure), FIG. 11 a schematic representation of the main steps of a method implemented by the control unit during a planning phase based on a pre-operative or pre-interventional image, then during the modeling phase (in the case where the lesion is not visible on the ultrasound images), FIG. 12 a schematic representation of an estimated movement of the patient marker during a breathing cycle of the patient, FIG. 13 a schematic representation of the tracking of the position of the patient marker over time, FIG. 14 a schematic representation of the real-time adjustment of the position of the robotic arm, based on the modelling of the position of the target point according to the position of the patient marker, FIG. 15 a schematic representation of the main steps of a method implemented by the control unit during a phase of insertion of the medical instrument.

In these figures, identical references from one figure to another denote identical or analogous elements. For reasons of clarity, the elements represented are not necessarily on the same scale, unless otherwise stated.

DETAILED DESCRIPTION OF AT LEAST ONE EMBODIMENT OF THE INVENTION

FIG. 1 diagrammatically shows a medical robot 10 according to the invention. The medical robot 10 is used to assist a practitioner during a medical intervention on an anatomy of interest of a patient 20 positioned on an intervention table 21.

By way of example, a medical intervention performed in a minimally invasive or percutaneous manner to treat a lesion within the anatomy of interest of the patient is considered. This type of intervention generally requires the insertion by the practitioner of one or more medical instruments (for example a needle, a probe, a catheter, etc.) into the patient's body to a certain depth in order to reach a target anatomical region (a lesion, for example a tumor) in the anatomy of interest (for example in the liver, a lung, a kidney, etc.).

The medical robot 10 comprises a base 11. In the example considered, the base 11 of the medical robot 10 is equipped with motorized wheels, which allow the medical robot 10 to move in different directions by translational and/or rotational movements.

The medical robot 10 further comprises an articulated robotic arm 13, one end of which is connected to the base 11. At the other end of the robotic arm 13 is fixed a tool guide 14 intended to guide a medical instrument 15, for example a needle, a probe, a catheter, an electrode, etc. The medical robot 10 can then be used to assist a practitioner in positioning, holding or guiding the medical instrument 15 during the medical intervention. The medical robot 10 then acts as a third hand for the practitioner.

The medical robot 10 comprises a control unit 12 configured to control the movement of the robotic arm 13. The control unit 12 comprises, for example, one or more processors 122 and a memory 121 (magnetic hard disk, electronic memory, optical disk, etc.) in which a computer program product is stored, in the form of a set of program code instructions to be executed in order to implement the various steps of a method for positioning the robotic arm 13. The memory 121 also makes it possible to record the images and other information (in particular the navigation information) used to implement this method.

The medical robot 10 may also comprise a user interface 19 comprising a display screen enabling the practitioner to view ultrasound images acquired by the ultrasound probe 40 or other medical images (for example a pre-operative or pre-interventional reference image of the anatomy of interest, or fusion images obtained from registering the ultrasound images with a reference image). The user interface can also comprise input means (keyboard, mouse, touch screen, etc.) enabling the practitioner to identify, on an image displayed on the display screen, a target point and/or an entry point and/or an anatomical region that is not to be traversed by the medical instrument 15.

In particular embodiments, the user interface can comprise an augmented reality device for superimposing the ultrasound images (or fusion images) with actual images of the patient's body on the display screen. Such a device facilitates the spatial representation of the anatomy of interest for the practitioner.

The medical robot 10 is configured to cooperate with a navigation system 30 and with an ultrasound probe 40 that is to be positioned by the practitioner at the anatomy of interest of the patient. The medical robot 10 comprises a communication module connected to the control unit 12 for exchanging data with the navigation system 30 and with the ultrasound probe 40. The navigation system 30 and the ultrasound probe 40 also each comprise a communication module for exchanging data with the control unit 12 of the medical robot 10. The communications established between the control unit 12, the navigation system 30 and the ultrasound probe may be wired communications or wireless communications. For the sake of simplification, the communication modules are not shown in FIG. 1.

In the example considered, the navigation system 30 is an optical navigation system. The navigation system 30 comprises two optical sensors 31 corresponding to two sensors of a stereoscopic camera operating in the infrared radiation range. In the example considered, the navigation system 30 further comprises a camera 32 operating in the visible light range.

The control unit 12 is configured to be able to determine at any time, from information communicated by the navigation system 30, the position of a robot marker 18 intended to be fixed on the medical robot 10, the position of a patient marker 22 intended to be positioned on the patient 20 in proximity to the anatomy of interest, and the position of a probe marker 41 intended to be fixed on the ultrasound probe 40.

In the present application, the term "position" corresponds to the combination of the position and the orientation of an object in a given frame of reference which is generally a three-dimensional coordinate system. The term "pose" is used in the English-language literature to represent this combination of the position and orientation of an object in space.

The control unit 12 is configured to receive, from the ultrasound probe 40, ultrasound images acquired by the ultrasound probe 40.

The ultrasound images received from the ultrasound probe 40 and the information received from the navigation system 30 are synchronized in time by the control unit 12 so as to be able to correlate the position of the lesion with the position of the patient marker 22 at a given instant.

Conventionally, the ultrasound probe 40 comprises one or more sound wave transmitter-receiver elements (piezoelectric materials, capacitive electronic transducers). The ultrasound probe produces ultrasonic waves by an indirect piezoelectric effect. Each time a wave encounters an anatomical structure, a part of this wave returns by reflection or scattering ("speckle") in the form of an echo. This echo is then transformed into electric current by a direct piezoelectric effect and then reconstructed into an image. The reconstruction of an ultrasound image depends mainly on the number, size and positions of the transmitter-receiver elements of the probe (lateral and longitudinal resolution), the duration of the emission pulses and the echo times (axial and/or depth resolution). The energy of the received echo is then encoded in gray level. The higher the energy, the whiter the corresponding image portion (pixel). This grayscale encoding is called "brightness", and the associated ultrasound mode is called "B-mode". The images produced by the ultrasound probe 40 may be two-dimensional images or three-dimensional images. Preferably, the ultrasound probe 40 is capable of generating images at a frequency of at least fifteen images per second.

The B-mode is particularly suitable when the anatomy of interest is the liver. However, it should be noted that the invention could also be used with other ultrasound modes, for example elastography.

In the example considered, and as illustrated in FIG. 2, the robotic arm 13 comprises six rotoid articulations 131 to 136 conferring six degrees of freedom, making it possible to position and/or move the medical instrument 15 in any position in the three-dimensional space. Advantageously, the articulations 131 to 135 of the robotic arm 13 are not aligned and are offset with respect to one another, which allows a greater number of possible configurations of the robotic arm 13. Each articulation comprises at least one encoder making it possible to know its angular position in real time. A configuration of the robotic arm 13 then corresponds to a set of parameter values taken by the articulations 131 to 136 (for example the value of an angle of rotation for each articulation). The rotoid articulation 136 corresponds to a rotation about the main axis of the tool guide 14. It should be noted, however, that it is not necessary to perform a rotation about the axis of symmetry of the medical instrument (five degrees of freedom are in fact sufficient to guide and release a medical instrument). This additional degree of freedom makes it possible to be in a redundancy situation and to have an infinite number of possible configurations of the robotic arm 13 for a given position of the tool guide 14. This redundancy situation is particularly useful in order to adapt to constraints related to the patient position or to the configuration of the operating theater. This redundancy situation makes it possible in particular to adapt to the external envelope of the patient and to the position of the markers; for example, if a configuration of the robotic arm hides one of the markers, it is possible to adopt another configuration of the robotic arm 13 while maintaining the same trajectory for the medical instrument 15.

In the example considered, and as illustrated in FIG. 3, the tool guide 14 is fixed to the robotic arm 13 by means of a flange 17. The tool guide comprises a main axis 145 represented in FIG. 3 by a dotted line. The tool guide 14 is coupled to a force sensor 16 to enable the control unit 12 to determine a force exerted on the tool guide 14. This force may in particular be exerted by the practitioner when he manually displaces the robotic arm 13. The force may also correspond to a force exerted on the tool guide 14 via the medical instrument 15 by the patient's body.

In the example considered, and as illustrated in FIGS. 4 and 5, the tool guide 14 comprises a body 141 with a base 142 intended to be fixed to the flange 17 by means of screws 143, and also a holding system 146 comprising two parts which can be moved relative to each other. The holding system 146 is intended to hold the medical instrument 15 at the end of the body 141 of the tool guide 14 opposite the base 142. The two mobile parts of the holding system 146 can be driven by a drive system such as a gear, a cam, a screw with reversed threads and/or a linear actuator, in order to lock or release the medical instrument 15. The linear actuator can be reversible (the holding system 146 of the tool guide 14 can then be opened manually or automatically on command of the control unit 12) or non-reversible (the holding system 146 of the tool guide 14 can only be opened automatically at the command of the control unit). The tool guide 14 makes it possible, for example, to guide medical instruments of different diameters. For example, such a guide makes it possible to guide medical instruments whose diameter is between 11 and 21 gauges. The gauge is a unit of measurement commonly used to define the external diameter of a medical instrument such as a needle, probe or catheter (11 gauges correspond to an external diameter of 2.946 mm; 21 gauges correspond to an external diameter of 0.812 mm).

As illustrated in FIGS. 4 and 5, the tool guide 14 comprises studs 144 intended to receive optical markers 181. Advantageously, the tool guide 14 comprises at least three optical markers 181 so that the position of the tool guide 14 can be determined in the three spatial dimensions of the reference frame of the navigation system 30. The respective positions of the optical markers 181 of the tool guide 14 relative to one another are known a priori by the navigation device 30 and/or by the control unit 12. Advantageously, the geometric shape of each optical marker 181 can also be known a priori. In the example illustrated in FIG. 5, the optical markers 181 are spherical in shape.

The set of optical markers 181 present on the tool guide 14 corresponds to the robot marker 18.

The use of at least three optical markers 181 makes it possible to define a plane and therefore a direct orthonormal three-dimensional reference frame with a z axis normal to the plane and x and y axes in the plane, so that the reference frame is direct. This thus makes it possible to determine the position and orientation of the reference frame formed from the optical markers 181 which represent the tool guide 14. The three axes x, y and z make it possible to define six degrees of freedom, namely a translation along each of the axes x, y or z and a rotation about each of these axes.

The optical markers 181 may be passive or active. Passive optical markers reflect optical radiation emitted by another element, such as for example the navigation system 30. Passive optical markers may correspond, for example, to reflecting spheres detectable by an infrared stereoscopic camera (this is what is used, for example, in the Polaris® navigation systems manufactured by Northern Digital Inc.), or to black and white patterns visible to a stereoscopic camera (this is what is used, for example, in the Micron-Tracker® navigation system from ClaroNav). Active optical markers themselves emit optical radiation, for example infrared radiation, detectable by the navigation system 30.

However, it should be noted that a single optical marker having a three-dimensional characteristic geometric shape could be used instead of the set of spherical optical markers 181.

FIG. 6 diagrammatically shows the patient marker 22 intended to be positioned on the patient 20 in proximity to the anatomy of interest. In the example considered, the patient marker 22 comprises four optical markers 23, so that the position of the patient marker 22 can be determined in the three spatial dimensions of the reference frame of the navigation system 30. The respective positions of the optical markers 23 of the patient marker 22 relative to one another are known a priori by the navigation system 30 and/or by the control unit 12. Advantageously, the geometric shape of each optical marker 23 can also be known a priori. In the example illustrated in FIG. 6, the optical markers 23 are spherical in shape. The spherical shape makes it possible to optimize the reflection of the optical radiation. What was mentioned above for the active or passive type of the optical markers 181 of the tool guide 14 is also true for the optical markers 23 of the patient reference 22. Here again, it would be conceivable to use a single optical marker having a three-dimensional characteristic geometric shape instead of the four spherical optical markers 23.

Optionally, and as illustrated in FIG. 6, the patient marker 22 may also comprise radiopaque markers 24 which are visible on a medical image acquired by a medical imaging device (for example by computed tomography, by magnetic resonance, by ultrasound, by tomography, by positron emission, etc.). The respective positions of the radiopaque markers 24 relative to one another are known a priori by the navigation device 30 and/or by the control unit 12. Advantageously, the geometric shape of the radiopaque markers 24 can also be known a priori. In the example considered, the patient marker 22 comprises four radiopaque markers 24. The radiopaque markers 24 may be ceramic beads, for example. It should however be noted that a single radiopaque marker having a characteristic geometric shape in three dimensions could be used instead of the four spherical radiopaque markers 24.

FIG. 7 diagrammatically shows the probe marker 41 intended to be fixed on the ultrasound probe 40 in order to enable the navigation system 30 to determine the position of the ultrasound probe 40. In the example considered, the probe marker 40 comprises three optical markers 42, so that the position of the probe marker 40 can be determined in the three spatial dimensions of the reference frame of the navigation system 30. The respective positions of the optical markers 42 of the probe marker 40 relative to one another are known a priori by the navigation system 30 and/or by the control unit 12. Advantageously, the geometric shape of each optical marker 42 can also be known a priori. In the example illustrated in FIG. 7, the optical markers 42 are spherical in shape. The spherical shape makes it possible to optimize the reflection of the optical radiation. What was mentioned above for the active or passive type of the optical markers 181 of the tool guide 14 is also true for the optical markers 42 of the probe reference 40. Here again, it would be possible to envisage using a single optical marker having a characteristic geometric shape in three dimensions instead of the three spherical optical markers 42.

In the remainder of the description, it is considered by way of non-limiting example that the optical sensors 31 of the navigation system 30 and the various optical markers 181, 23, 42 are designed to operate with infrared type optical radiation. It is also considered that the optical markers 181, 23, 42 are passive markers. The optical sensors 31 are configured to emit infrared radiation. This infrared radiation is reflected by the various optical markers 181, 23, 42 toward the optical sensors 31. The optical sensors 31 are configured to receive the reflected infrared radiation. The navigation system 30 can then determine the distance between an optical marker 181, 23, 42 and an optical sensor 31 by measuring the time taken by an infrared ray to make the round trip between said optical sensor 31 and said optical marker 181, 23, 42. Knowing the distance between each optical marker 181, 23, 42 and each optical sensor 31, and knowing a priori the arrangement of the optical markers 181, 23, 42 with respect to one another on the robot marker 18, on the patient marker 22, and on the probe marker 41, it is possible to determine the position of the robot marker 18, of the patient marker 22, and of the probe marker 41 in the reference frame of the navigation system 30. It should be noted that optical navigation by infrared is a well-known method in the field of surgical interventions assisted by a medical robot.

It should be noted that the invention is described using an optical navigation system. However, nothing would prevent the use, in a variant, of an electromagnetic navigation system in place of the optical navigation system. In this case, the various "markers" detectable by the navigation system (patient marker 22, robot marker 18, and probe marker 41) would then correspond to electromagnetic sensors whose position can be determined by the navigation system in a generated electromagnetic field.

In the example considered, the control unit 12 of the medical robot 10 is configured to receive from the navigation system 30 information on the current position of the robot marker 18 in the reference frame of the navigation system 30. Now, the control unit 12 of the medical robot 10 knows the current position of the robot marker 18 in the reference frame of the medical robot 10 (via the encoders of the articulations 131 to 136). The control unit 12 can therefore determine the transformation to be carried out in order to define a position in the reference frame of the medical robot 10 from a position in the reference frame of the navigation device 30.

The control unit 12 is also configured to receive from the navigation system 30 information on the position of the patient marker 22 and on the position of the probe marker 41 in the reference frame of the navigation system 30. The control unit 10 can then define the position of the patient marker 22 and the position of the probe marker 41 in the reference frame of the medical robot 10.

When the position of the probe marker 41 is known at a given time, it is possible to determine the position of a visible element on an ultrasound image acquired by the ultrasound probe 40 at that time. This visible element may be, in particular, a target point to be reached at the lesion to be treated or an entry point of the medical instrument at the patient's skin. The target point and the entry point define a trajectory to be followed by the medical instrument 15. When the position of the target point and the position of the entry point are known, i.e. when the trajectory to be followed by the medical instrument 15 is defined, the control unit can automatically move the robotic arm 13 into a configuration that allows the tool guide 14 to guide the medical instrument 15 along the defined trajectory.

However, and as explained above, the movements related to the patient's breathing may cause a displacement of the target point. Thus, the trajectory that the medical instrument 15 must follow at a given instant of the patient's respiratory cycle is not the same at another instant of the respiratory cycle.

To solve this problem, the control unit 12 is configured to model, during a modeling phase which precedes the surgical procedure, the movement of the patient marker 22 during at least one respiratory cycle of the patient 20. During the modeling phase, the position of the target point and the position of the entry point are correlated to the position of the patient marker 22. It is thus possible to define the position of the target point and the position of the entry point according to the position of the patient marker. The modeling obtained therefore makes it possible to define, from the position of the patient marker 22, and at any instant of the respiratory cycle, the position of the target point and the position of the entry point which correspond to the trajectory to be followed by the medical instrument 15 in order to accurately reach the target point.

Once the position of the target point and the position of the entry point are modeled as a function of the position of the patient marker 22, it becomes possible, by tracking in real time the position of the patient marker 22 with the aid of the navigation system 30, to define in real time the position that the robotic arm 13 must take so that the medical instrument 15 is guided along the trajectory defined by the position of the target point and the position of the entry point associated with the position of the patient marker 22. This real-time tracking may in particular take place during a guidance phase, before the insertion of the medical instrument 15. The robotic arm 13 is moved in real time so that the position of the robotic arm is constantly adjusted to guide the medical instrument along the desired trajectory.

FIG. 8 diagrammatically represents the main steps of a method implemented by the control unit 12 during a modeling phase, then during a phase of real-time control of the robotic arm, before the insertion of the medical instrument 15.

During the modeling phase, the control unit 12 is configured to receive a plurality of ultrasound images acquired by the ultrasound probe 40 during at least one respiratory cycle of the patient 20. The following steps are therefore repeated throughout the modeling phase:

acquisition 201 of an ultrasound image (the ultrasound image corresponds to an analysis image on which the lesion is visible), determination 202 of the position of the patient marker 22 and of the position of the probe marker 41 at the instant at which said ultrasound image was acquired by the ultrasound probe 40, determination 204, on the analysis image, of a target point at the lesion and an entry point at the patient's skin 20 (the target point and the entry point define a trajectory to be followed for the medical instrument 15), determination 205 of the position of the target point and the position of the entry point from the position of the probe marker 41, association 206 between the position of the patient marker 22, the position of the target point and the position of the entry point thus determined for said ultrasound image.

At the end of the modeling phase, the control unit 12 is configured to carry out, on the basis of the information thus obtained for the various ultrasound images, a modeling 207 of the position of the target point and of the position of the entry point, as a function of the position of the patient marker 22, irrespective of the moment considered in a respiratory cycle of the patient.

Then, during the guidance phase, the control unit 12 is configured to control the robotic arm 13 in real time. For this purpose, at each instant, the following steps are carried out by the control unit 12:

determination 301 of the position of the patient marker 22, determination 302, using the modelling, of the position of the target point and the position of the entry point associated with the position of the patient marker 22, displacement 303 of the robotic arm 13 in order to adjust the position of the tool guide 14 so that the medical instrument 15 is guided by the tool guide 14 according to the trajectory defined by the position of the target point and the position of the entry point thus determined.

A first determination of a target point at the lesion and of an entry point at the patient's skin is for example initially carried out on a first analysis image. Then, subsequently, an algorithm for tracking movement in several successive analysis images can be implemented to determine the target point and the entry point on each new analysis image, for example with the aid of a deformation analysis of the speckle (a set of fluctuating spots on the images due to wave scattering) or by an artificial intelligence algorithm.

The first determination of a target point and of an entry point can be carried out by the practitioner using the graphical interface 19. FIG. 9 illustrates a user interface enabling the practitioner to identify on an analysis image a target point 51 at the region to be treated 50, and/or an entry point 52 at the skin of the patient, and/or a risk zone to be avoided (for example the bones or blood vessels), and also treatment parameters. This step can be facilitated by segmentation of certain anatomical regions (anatomy of interest, lesion to be treated, risk zones, etc.) by a machine learning algorithm.

Alternatively, the first determination of a target point and of an entry point may be implemented automatically by an artificial intelligence algorithm.

However, it is possible that the lesion to be treated is not visible on an ultrasound image, for example because the nature of the lesion means that it is not visible (or is only barely visible) on an ultrasound image. In this case, use should be made of a pre-interventional reference image (i.e. an image acquired just before or at the start of the intervention) or a pre-operative image (i.e. an image acquired several days or weeks before the intervention) on which the lesion is visible. This may in particular be a computed tomography image, a positron emission tomography image or a magnetic resonance imaging image. The reference image may be a two-dimensional image or a three-dimensional image. The first determination of a target point and of an entry point can then be performed on the reference image instead of being performed on a first ultrasound image. Here again, the first determination of a target point and of an entry point can be carried out by the practitioner (for example by means of the graphical interface 19 illustrated in FIG. 9) or else automatically by an artificial intelligence algorithm. An ultrasound image acquired by the ultrasound probe 40 can then be registered with the reference image in order to form an analysis image corresponding to the merging of the reference image with the ultrasound image. The target point and the entry point are then visible on the analysis image.

Alternatively, the first determination of a target point and of an entry point may be carried out on a first analysis image instead of being carried out on the reference image.

FIG. 10 schematically illustrates the use of a pre-operative or pre-interventional reference image (part a) of FIG. 10) for registering an ultrasound image (part b) of FIG. 10) in order to form an analysis image (part c) of FIG. 10) resulting from the registration and merging of the reference image with the ultrasound image. The lesion to be treated 50 and the target point 51 are visible on the reference image. In the example considered, the reference image is acquired by computed tomography. On the other hand, the lesion to be treated 50 is barely visible on the ultrasound image. The lesion to be treated 50 and the target point 51 become visible on the analysis image resulting from the registration of the reference image with the ultrasound image.

The registration is for example implemented by the control unit 12 with the aid of an automatic learning algorithm trained to register globally (registration on the whole of the anatomy) or locally (optimized on a zone of interest), in a rigid manner (translation and rotation) or non-rigid manner (deformation), a computed tomography image of an anatomy of interest with an ultrasound image. The image resulting from this registration is called the analysis image or the fusion image.

If radiopaque elements of the patient marker 22 are visible on the reference image, a rigid registration can also be based on the position of the patient marker 22 relative to the position of the probe marker 41 at the instant at which the ultrasound image was acquired by the ultrasound probe 40.

FIG. 11 schematically represents the main steps implemented during a planning phase based on a pre-operative or pre-interventional reference image, then during the modeling phase, in the case where the lesion is not visible on the ultrasound images.

The planning phase comprises in particular a step of acquisition 101 of a pre-operative or pre-interventional reference image and then a step 102 of determining the target point 51 and the entry point 52 on the reference image.

The modeling phase comprises substantially the same steps as those described with reference to FIG. 8. For each ultrasound image received during the modeling phase, the control unit 12 is further configured to implement a step 203 of generating an analysis image by registering the ultrasound image with the reference image. The determination 204 of the target point and of the entry point is then carried out on this analysis image resulting from the registration of the ultrasound image with the reference image (whereas in the case of FIG. 8 the analysis image corresponds directly to the ultrasound image).

When the lesion is not visible on the ultrasound image, in order to assist in tracking the target point on the analysis images, it may be advantageous to track the movement of an anatomical structure close to the lesion and visible on the ultrasound images (for example a blood vessel).

It should be noted that step 102 may be optional if the first determination of the target point and of the entry point is performed on a first analysis image instead of being performed on the reference image.

Once the target point 51 and the entry point 52 have been determined on an analysis image, their respective positions can be determined by rigid registration in the reference frame of the navigation system 30, or in the reference frame of the medical robot 10, by virtue of the known position of the probe marker 41 relative to the position of the transmitter-receiver elements of the ultrasound probe 40.

FIGS. 12 to 14 illustrate the step 207 of modeling the position of the target point 51 and of the entry point 52 as a function of the position of the patient marker 22.

FIG. 12 shows, by way of example, a recording of the movement followed by the patient marker 22 during a period of recording a predetermined duration corresponding to several respiratory cycles of the patient. Each point corresponds to a position taken by the patient marker 22 in the course of time in a plane XY of a coordinate system of the navigation system 30 (the movement of the patient marker 22 could also be represented in the reference frame of the medical robot 10). In this example, it can be seen that the movement of the patient marker 22 takes place mainly along an axis 54.

The movement of the patient marker 22 is representative of the movement of the patient's rib cage caused by the patient's breathing. For a better interpretation of the movement of the marker, and by analogy to the respiratory cycle of the patient, it is preferable to obtain a one-dimensional curve illustrating the oscillatory movement of the marker over time. There are different methods for obtaining this one-dimensional curve. For example, it is conceivable to consider that the movement of the marker is predominantly vertical, and consequently to consider only the Y axis. However, in this case, part of the amplitude of the movement of the marker is lost. According to another example, it is conceivable to carry out a key component analysis of the positions of the marker. The positions of the marker may in particular be displayed along a key component corresponding to the main axis 54 of the movement of the marker.

FIG. 13 shows a curve 55 describing the movement of the patient marker 22 over time, during the recording period, along the main axis 54. The position $(M_P)$ of the patient marker 22 along the axis 54 is shown on the ordinate; the time (t) is shown on the abscissa. The recording period comprises several respiratory cycles of the patient 20.

As illustrated in FIG. 13, a high position of the rib cage of the patient 20 corresponds to the end of an inspiration in a respiratory cycle. This also corresponds to a maximum of the curve 55 describing the position of the patient marker 22 over time. A low position of the rib cage of the patient 20 corresponds to the end of an expiration in a respiratory cycle. This also corresponds to a minimum of the curve 55 describing the position of the patient marker 22 over time.

During the modeling phase, the control unit 12 determines for each analysis image the position of the target point, the position of the entry point and the position of the patient marker. These positions can then be correlated in order to model the position of the target point and the position of the entry point over time as a function of the position of the patient marker.

FIG. 14 illustrates, by way of example, a model 56 of the position of the target point (C) as a function of the position of the patient marker ($M_P$) during an inspiration period of a respiratory cycle.

By modeling the position of the target point and the position of the entry point over time based on the position of the patient marker, it becomes possible to determine in real time the configuration that the robotic arm 13 must take so that the tool guide 14 is constantly positioned in such a way that the medical instrument 15 is guided by the tool guide 14 along the trajectory defined by the position of the target point and the position of the entry point. This real-time adjustment 303 of the position of the robotic arm 13 can be carried out simply by tracking in real time the position of the patient marker 22 and by using the model making it possible to estimate the position of the target point and the position of the entry point as a function of the position of the patient marker. It is then no longer necessary to acquire ultrasound images in order to adjust in real time the position of the robotic arm 13 during the guidance phase.

Thus, it becomes possible to block the patient's breathing at any time during the respiratory cycle so as to proceed with the insertion of the medical instrument. Indeed, irrespective of the time at which the patient's breathing is blocked, the robotic arm will be correctly positioned in order to allow the insertion of the medical instrument along the desired trajectory.

It is no longer necessary to block the patient's breathing during the intervention. Indeed, the phase of guiding the robotic arm with the aid of the model can be continued during the insertion of the medical instrument. The robotic arm is then controlled in real time such that the position of the robotic arm is constantly adjusted in order to guide the medical instrument along the desired trajectory. However, it should be noted that, during the insertion of the medical instrument, the position of the entry point at the patient's skin is fixed and becomes a pivot of rotation for the movements of the robotic arm.

The guidance phase can be carried out based entirely on the model generated during the modeling phase. It is therefore not necessary for ultrasound images to be acquired during the guidance phase.

However, it may be advantageous to take into account any displacement of the target point resulting from the insertion of the medical instrument. The target point can in fact move in the direction of the trajectory followed by the medical instrument during its insertion (this is particularly the case when the target point to be reached is in a lesion, for example a tumor, within a soft organ). It is then conceivable to update in real time the model making it possible to estimate the position of the target point in order to adjust the trajectory to be followed by the medical instrument, and also the position of the robotic arm in order to guide the medical instrument along this trajectory.

FIG. 15 diagrammatically shows the main steps of a method implemented by the control unit 12 during a guidance phase during the insertion of the medical instrument 15. The control unit 12 is configured to receive new ultrasound images acquired by the ultrasound probe 40. The following steps are therefore repeated for each new image:

acquisition 401 of an ultrasound image, determination 402 of the position of the patient marker 22 and of the position of the probe marker 41 at the instant at which said ultrasound image was acquired by the ultrasound probe 40, generation 403 of an analysis image from the ultrasound image and the reference image (it is noted that this step is optional if the lesion is directly visible on the ultrasound image), determination 404, from the analysis image and the position of the probe marker 41, of the position of the target point, the position of the entry point, and the position of the medical instrument 15, updating 405 of the model initially generated during the modeling phase, adjustment 406 of the position of the robotic arm 13 based on the updated model.

The determination of the position of the medical instrument for each new ultrasound image received also makes it possible to detect any curvature of the medical instrument during insertion, and if necessary to adjust the real-time control of the robotic arm accordingly.

If the ultrasound probe 40 is not positioned correctly, the lesion may not be in the field of view of the ultrasound probe. It is then expedient to be able to provide the practitioner with information on a direction in which the ultrasound probe must be moved so that the lesion is in the field of view of the ultrasound probe.

To this end, the control unit 12 can be configured to compare an ultrasound image with a reference image on which the lesion is visible, and to give an indication to the practitioner of the direction in which the ultrasound probe 40 should be moved so that an ultrasound image acquired by the ultrasound probe 40 comprises an anatomical region in which the lesion is located. This indication may, for example, be provided by light indicators or by a haptic feedback module of the ultrasound probe. Alternatively, this indication can be provided to the practitioner via the graphical interface 19.

The above description clearly illustrates that, by virtue of their various features and their advantages, the devices and methods presented achieve the objectives set.

In particular, the medical robot 10 uses the breathing information to position the tool guide 14 so as to follow the position of the lesion with precision and in real time, without specific manipulation by the practitioner.

During the insertion of the medical instrument 15, the lesion (in particular in the soft organs) can move in the direction of the trajectory. By determining the position of the lesion in the ultrasound images in real time and by correlating it with the position of the patient marker 22, the trajectory of the medical instrument 15 inserted by the robotic arm can be updated in real time. Lateral trajectory readjustments (which are usually traumatic for the anatomy of interest) are minimized. By tracking the position of the medical instrument during its insertion, it is possible to compensate for any curvature of the medical instrument.

The real-time control of the position of the robotic arm 13 is performed by means of ultrasound images. Therefore, the patient and the medical personnel are not exposed to ionizing radiation during the intervention.

A lesion that is barely visible or not visible on ultrasound images can be detected by registration using the imaging modality that provides the best visibility.

The invention claimed is:

1. A medical robot for assisting a practitioner during a medical intervention for treating a lesion in an anatomy of interest of a patient, said medical robot comprising a robotic arm comprising at a distal end a tool guide intended to guide a medical instrument, and a control unit configured to control the robotic arm, the medical robot being configured to cooperate with a navigation system and with an ultrasound probe to be positioned by the practitioner at the anatomy of interest of the patient, the control unit being configured to be able to determine at any time, on the basis of information communicated by the navigation system, the position of a robot marker to be attached to the medical robot, the position of a patient marker to be positioned on the patient in the vicinity of the anatomy of interest, and the position of a probe marker to be attached to the ultrasound probe, wherein during a modeling phase, the control unit is configured to receive a plurality of ultrasound images acquired by the ultrasound probe during at least one respiratory cycle of the patient and to generate, from said ultrasound images, a model for estimating the position of a target point at the lesion and the position of an entry point at the skin of the patient, irrespective of a particular moment of the patient's subsequent respiratory cycle, based on the position of the patient marker at that particular moment, and during a guidance phase, the control unit is configured to control the robotic arm in real time based on the position of the patient marker such that the tool guide makes it possible to guide the medical instrument along a trajectory defined by the position of the target point and the position of the entry point associated with the position of the patient marker in the model without the need to acquire an ultrasound image at that particular moment.

2. The medical robot of claim 1, wherein, during the modeling phase, the control unit is configured to:

for each ultrasound image received:

determine the position of the patient marker and the position of the probe marker at the time that said ultrasound image was acquired by the ultrasound probe, obtain an analysis image, from the ultrasound image, on which the lesion is visible, determine, on the analysis image, a target point at the lesion and an entry point at the skin of the patient, the target point and the entry point thus defining a trajectory to be followed for the medical instrument, determine the position of the target point and the position of the entry point from the position of the probe marker, and establish an association between the position of the patient marker, the position of the target point and the position of the entry point thus determined for said ultrasound image, and to model, from the association between the position of the patient marker, the position of the target point and the position of the entry point determined for each of the plurality of ultrasound images, the position of the target point and the position of the entry point, as a function of the position of the patient marker, irrespective of the particular moment in a respiratory cycle of the patient.

3. The medical robot of claim 2, wherein the analysis image is the ultrasound image, the lesion being visible on the ultrasound image.

4. The medical robot of claim 2, wherein the control unit is configured to obtain the analysis image by merging the ultrasound image with a pre-operative or pre-interventional reference image on which the lesion is visible.

5. The medical robot of claim 4, wherein a radiopaque element of the patient marker is visible on the reference image, and the control unit is configured to merge the ultrasound image with the reference image by registration based on the position of the patient marker relative to the position of the probe marker at the time when the ultrasound image was acquired by the ultrasound probe.

6. The medical robot of claim 4, wherein the reference image is a computed tomography image, a positron emission tomography image or a magnetic resonance imaging image.

7. The medical robot of claim 2, further comprising a user interface comprising a display screen enabling the practitioner to view the analysis images.

8. The medical robot of claim 7, wherein the user interface comprises input means enabling the practitioner to identify, on an analysis image displayed on the display screen, a target point and/or an entry point and/or an anatomical region that is not to be traversed by the medical instrument.

9. The medical robot of claim 7, wherein the user interface comprises an augmented reality device for superimposing the analysis images with actual images of the patient's body on the display screen.

10. The medical robot of claim 1, wherein, during the guiding phase, upon insertion of the medical instrument, the control unit is configured to regularly receive new ultrasound images acquired by the ultrasound probe and to update the model based on said new ultrasound images.

11. The medical robot of claim 10, wherein, during the guiding phase, upon insertion of the medical instrument, the control unit is further configured to determine, for each new received ultrasound image, the position of the medical instrument, and to adjust the real-time control of the robotic arm based on the position of the medical instrument.

12. The medical robot of claim 1, wherein the ultrasound images received from the ultrasound probe are B-mode ultrasound images.

13. The medical robot of claim 1, wherein the control unit is configured to receive and process ultrasound images acquired by the ultrasound probe at a rate of at least fifteen images per second.

14. The medical robot of claim 1, wherein the control unit is configured to compare an ultrasound image with a reference image on which the lesion is visible, and to give an indication to the practitioner of the direction in which the ultrasound probe should be moved so that an ultrasound image acquired by the ultrasound probe comprises an anatomical region in which the lesion is located.

15. A medical device comprising a medical robot of claim 1, and a navigation system and an ultrasound probe for cooperating with the medical robot.

\* \* \* \* \*